(12) United States Patent
Payton et al.

(10) Patent No.: US 10,918,821 B2
(45) Date of Patent: Feb. 16, 2021

(54) BREATHING ASSISTANCE APPARATUS

(71) Applicant: Fisher & Paykel Healthcare Limited, Auckland (NZ)

(72) Inventors: Matthew Jon Payton, Auckland (NZ); Kevin Peter O'Donnell, Auckland (NZ); Christopher Simon James Quill, Auckland (NZ); Ian Douglas Makinson, Auckland (NZ); Emily Joy Drake, Auckland (NZ); Craig Karl White, Auckland (NZ); Virigina Louise Owen, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 688 days.

(21) Appl. No.: 15/811,308

(22) Filed: Nov. 13, 2017

(65) Prior Publication Data
US 2018/0161536 A1    Jun. 14, 2018

Related U.S. Application Data

(63) Continuation of application No. 14/919,459, filed on Oct. 21, 2015, now Pat. No. 9,839,759, which is a (Continued)

(30) Foreign Application Priority Data

May 26, 2005  (NZ) .................................... 540402

(51) Int. Cl.
*A61M 16/16*    (2006.01)
*A61M 16/00*    (2006.01)
(Continued)

(52) U.S. Cl.
CPC ...... *A61M 16/161* (2014.02); *A61M 16/0003* (2014.02); *A61M 16/0006* (2014.02);
(Continued)

(58) Field of Classification Search
None
See application file for complete search history.

(56) References Cited

U.S. PATENT DOCUMENTS

| 4,391,271 | A | 7/1983 | Blanco |
| 4,955,372 | A | 9/1990 | Blackmer et al. |

(Continued)

FOREIGN PATENT DOCUMENTS

| GB | 2338420 | 12/1999 |
| JP | H04-54968 | 2/1992 |

(Continued)

OTHER PUBLICATIONS

Canadian Examination Report for application No. 2609738; dated Apr. 23, 2012, 3 pages.
(Continued)

*Primary Examiner* — Rachel T Sippel
(74) *Attorney, Agent, or Firm* — Knobbe Martens Olson and Bear, LLP

(57) ABSTRACT

A breathing assistance apparatus and method of controlling a breathing assistance apparatus is disclosed. Particularly, the breathing assistance apparatus is controlled such that it has a drying cycle to enable drying of the tubing that supplies gases to a user and prevent the harbouring of pathogens within the tube. The drying cycle is preferably operated automatically by internal controllers in the apparatus. However, it may be manually activated by pressing a button on the apparatus. The drying cycle is preferably activated at the end of a user's treatment session.

18 Claims, 2 Drawing Sheets

Related U.S. Application Data continuation of application No. 14/522,416, filed on Oct. 23, 2014, now Pat. No. 9,168,350, which is a continuation of application No. 11/913,812, filed as application No. PCT/NZ2006/000132 on May 26, 2006, now Pat. No. 8,893,715.

(51) Int. Cl.
*A61M 16/10* (2006.01)
*A61M 16/06* (2006.01)
*A61M 16/08* (2006.01)

(52) U.S. Cl.
CPC ...... *A61M 16/009* (2013.01); *A61M 16/0066* (2013.01); *A61M 16/0069* (2014.02); *A61M 16/024* (2017.08); *A61M 16/0666* (2013.01); *A61M 16/0875* (2013.01); *A61M 16/109* (2014.02); *A61M 16/1075* (2013.01); *A61M 16/1095* (2014.02); *A61M 16/16* (2013.01); *A61M 16/0683* (2013.01); *A61M 2016/003* (2013.01); *A61M 2205/3303* (2013.01); *A61M 2205/3368* (2013.01); *A61M 2205/36* (2013.01); *A61M 2205/50* (2013.01); *A61M 2230/40* (2013.01)

(56) References Cited

U.S. PATENT DOCUMENTS

| | | | |
|---|---|---|---|
| 5,551,419 A | 9/1996 | Froehlich | |
| 5,558,084 A | 9/1996 | Daniell et al. | |
| 5,862,802 A | 1/1999 | Bird | |
| 6,240,921 B1 | 6/2001 | Brydon et al. | |
| 6,523,538 B1 | 2/2003 | Wikefeldt | |
| 6,895,803 B2 | 5/2005 | Seakins et al. | |
| 7,111,624 B2 | 9/2006 | Thurdor et al. | |
| 7,140,367 B2 | 11/2006 | White et al. | |
| 7,802,569 B2 | 9/2010 | Yeates et al. | |
| 7,882,834 B2 | 2/2011 | Gradon et al. | |
| 8,453,641 B2 | 6/2013 | Payton et al. | |
| 8,733,353 B2 | 5/2014 | Kramer et al. | |
| 8,893,715 B2 | 11/2014 | Payton | |
| 9,168,350 B2 | 10/2015 | Payton et al. | |
| 9,180,266 B1* | 11/2015 | Sherman | A61M 16/0003 |
| 9,839,759 B2 | 12/2017 | Payton et al. | |
| 2003/0094178 A1* | 5/2003 | McAuley | A61M 16/0666 128/207.18 |
| 2003/0154977 A1 | 8/2003 | White et al. | |
| 2004/0149284 A1 | 8/2004 | Smith et al. | |
| 2004/0221844 A1 | 11/2004 | Hunt et al. | |
| 2006/0027234 A1 | 2/2006 | Gradon et al. | |
| 2007/0144514 A1 | 6/2007 | Yeates et al. | |
| 2008/0028850 A1 | 2/2008 | Payton et al. | |
| 2008/0196722 A1 | 2/2008 | Kramer et al. | |
| 2008/0092898 A1* | 4/2008 | Schneider | A61M 16/0858 128/206.28 |
| 2008/0310994 A1 | 12/2008 | O'Donnell et al. | |
| 2009/0071478 A1 | 3/2009 | Kalfon | |
| 2012/0037156 A9 | 2/2012 | Tatkov et al. | |
| 2012/0048271 A1 | 3/2012 | O'Donnell et al. | |

FOREIGN PATENT DOCUMENTS

| | | |
|---|---|---|
| WO | WO 2001/013981 | 3/2001 |
| WO | WO 2001/49351 | 7/2001 |
| WO | WO 02/02169 | 1/2002 |
| WO | WO 02/32486 | 4/2002 |
| WO | WO 2004/020031 | 3/2004 |
| WO | WO 2004/112873 | 12/2004 |
| WO | WO 2006/015416 | 2/2006 |

OTHER PUBLICATIONS

European Examination Report for application No. 06747709.1; dated Jan. 31, 2013 in 5 pages.
International Search Report and Written Opinion dated Oct. 16, 2009 in the PCT International Application No. PCT/NZ2009/000091.
Melikov, A. K. et al. "Accuracy Limitations for Low-Velocity Measurements and Draft Assessment Rooms" *HVAC & R Research* 13(6), Nov. 2007.
India Examination Report for application No. 4105/KOLNP/2007; dated Oct. 28, 2015; 2 pages.

* cited by examiner

BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This invention relates to a breathing gases supply and gases humidification apparatus and a method of controlling such apparatus. Uses for the breathing assistance apparatus of the present invention are the supply of gases for any medical condition or treatment that results in the drying of the upper airways, and/or salivary glands, such as head or neck radiotherapy or long term oxygen therapy. Further uses are for medical conditions that result in impaired mucociliary clearance systems such as Chronic Obstructive Pulmonary Disease (COPD) or bronchiectasis or in the supply of Continuous Positive Airway Pressure (CPAP) to treat Obstructive Sleep Apnoea (OSA) or other respiratory conditions.

Description of the Related Art

A number of methods are known in the art for assisting a patient's breathing. Continuous Positive Airway Pressure (CPAP) involves the administration of air under pressure to a patient, usually by a nasal mask. It is used in the treatment of snoring and Obstructive Sleep Apnoea (OSA), a condition characterised by repetitive collapse of the upper airway during inspiration. Positive pressure splints the upper airway open, preventing its collapse. Treatment of OSA with nasal CPAP has proven to be both effective and safe, but CPAP is difficult to use and the majority of patients experience significant side effects, particularly in the early stages of treatment.

CPAP is also commonly used for patients with a variety of respiratory illnesses, including COPD.

Upper airway symptoms adversely affect treatment with CPAP. Mucosal drying is uncomfortable and may awaken patients during the night. Rebound nasal congestion commonly occurs during the following day, simulating a viral infection. If untreated, upper airway symptoms adversely affect rates of CPAP use.

Increases in nasal resistance may affect the level of CPAP treatment delivered to the pharynx, and reduce the effectiveness of treatment. An individual pressure is determined for each patient using CPAP and this pressure is set at the patient interface. Changes in nasal resistance affect pressure delivered to the pharynx and if the changes are of sufficient magnitude there may be recurrence of snoring or airway collapse or reduce the level of pressure applied to the lungs. Such symptoms can also occur in a hospital environment where a patient is on a respirator. Typically in such situations the patient is intubated. Therefore the throat tissue may become irritated and inflamed causing both distress to the patient and possible further respiratory problems.

A number of methods may be employed to treat such upper airway symptoms, including pharmacological agents to reduce nasal disease, or heating the bedroom. One most commonly employed method is humidification of the inspired air using an in line humidifier. Two types of humidifier are currently used. Cold pass-over humidifiers rely on humidifying the air through exposure to a large surface area of water. While they are cheap, the humidity output is low at high flows, typically 2 to 4 mgL absolute humidity at flows above 25 L/min. The output is insufficient to prevent mucosal drying. Heated water bath humidifiers are more efficient, and produce high levels of humidity even at high flow rates. They are effective at preventing upper airway mucosal drying, prevent increases in nasal resistance, and are the most reliable means of treating upper airway symptoms.

Oxygen is the most common drug prescribed to hospitalized patients. The delivery of oxygen via nasal cannula or facemask is of benefit to a patient complaining of breathlessness. By increasing the fraction of inspired oxygen, oxygen therapy reduces the effort to breathe and can correct resulting hypoxia (a low level of oxygen in the tissues).

The duration of the therapy depends on the underlying illness. For example, postoperative patients may only receive oxygen while recovering from surgery while patients with COPD require oxygen 16 to 18 hours per day.

Currently greater than 16 million adults are afflicted with COPD, an umbrella term which describes a group of lung diseases characterized by irreversible airflow limitation that is associated mainly with emphysema and chronic bronchitis, most commonly caused by smoking over several decades. When airway limitation is moderately advanced, it manifests as perpetual breathlessness, without physical exertion. Situations such as a tracheobronchial infection, heart failure and also environmental exposure can incite an exacerbation of COPD that requires hospitalization until the acute breathlessness is under control. During an acute exacerbation of COPD, the patient experiences an increase in difficulty of breathing (dyspnea), hypoxia, and increase in sputum volume and purulence and increased coughing.

Oxygen therapy provides enormous benefit to patients with an acute exacerbation of COPD who are hypoxic, by decreasing the risk of vital organ failure and reducing dyspnea. The major complication associated with oxygen therapy is hypercarpnia (an elevation in blood carbon dioxide levels) and subsequent respiratory failure. Therefore, the dose of oxygen administered can be critical and must be precisely known.

To accurately control the oxygen dose given to a patient, the oxygen-enriched gas must exceed the patient's peak inspiratory flow to prevent the entrainment of room air and dilution of the oxygen. To achieve this, flows of greater than 20 L/min are common. Such flows of dry gases cause dehydration and inflammation of the nasal passages and airways if delivered by nasal cannula. To avoid this occurrence, a heated humidifier is used.

The majority of systems that are used for oxygen therapy or merely delivery of gases to a patient consists of a gases supply, a humidifier and conduit. Interfaces include face masks, oral mouthpieces, tracheostomy inlets and nasal cannula, the latter having the advantage of being more comfortable and acceptable than a facemask.

It is usual for the gases supply to provide a constant, prescribed level of gases flow to the humidifier. The humidifier and conduit can then heat and humidify the gases to a set temperature and humidity before delivery to the patient. It is important to note that the warm-up time required from start-up for the gases to reach optimal temperature and humidity increases with higher flow rates. The operating instructions of such a system commonly instruct the user not to connect the system to the patient until the humidifier has completed the warm-up period. Thereafter, patients receive up to 40 L/min of near body temperature saturated gases. Patients often feel overwhelmed by sudden delivery of high flow at this time.

A group of patients who would benefit from humidification therapy are patients who have mucociliary clearance deficiencies. These patients often have purulent mucus and are susceptible to infections from pathogens. Heated humidified air with an abundance of water particles is an ideal medium to harbour disease carrying pathogens. Consequently, considerable design expertise has been required to provide the market with active pass-over humidifiers that deliver water molecules, in gas phase only, so that it is not possible for disease pathogens to be carried in air to the patient. Water that condenses on the inner surfaces of the breathing circuit or conduit at the end of a treatment session may harbour pathogens that would be delivered to the patient next time they use the device. This is particularly the case with therapies for COPD patients that are receiving body temperature fully saturated air.

The hygiene of a breathing circuit (the tubing supplying humidified gases to a patient) is particularly important when the humidification therapy is used for the treatment of respiratory diseases. Any moisture remaining in the breathing circuit at the end of a treatment may harbour pathogens exhaled or expelled (as mucus may be expelled into the circuit or patient interface) by the patient. This moisture provides a means to transport the pathogens in the tubing providing a source of further infection for the patient when the tubing is next used. Often with such treatment the tubing is not cleaned daily and therefore must be thoroughly dried at the end of treatment. This cleaning is time consuming and will not always be carried out to precise instructions.

SUMMARY OF THE INVENTION

It is an object of the present invention to provide a breathing assistance apparatus which goes some way to overcoming the abovementioned disadvantages or which at least provides the public or industry with a useful choice.

Accordingly in a first aspect the present invention consists in a breathing assistance apparatus adapted to deliver humidified gases at a desired level of humidity, flow and temperature for treatment of a patient comprising: a) gases supply means providing a flow of gases, b) a humidifier having a chamber adapted to receive a volume of water and a chamber heater to heat said water in said chamber, said chamber including an inlet and an outlet, c) transportation pathway means to convey said humidified gases from said humidifier to said patient, d) a controller having stored instructions to complete the following steps at the end of said treatment of said patient: i) switch off power to said chamber heater, ii) set said flow of gases from said gases supply means to a predetermined flow for a predetermined time, iii) after said predetermined time switch off said gases supply means.

Preferably said transportation pathway means has a pathway heater, and said apparatus further comprises: a) an outlet temperature sensor measuring the temperature of said gases at said outlet to said chamber, b) a distal temperature sensor measuring the temperature of said gases at the distal end of the transportation pathway means, c) an ambient temperature sensor measuring ambient air temperature, and said controller includes stored instructions to: i) control said pathway heater over said predetermined time such that the temperature of said gases at the distal end of said transportation pathway means, as sensed by said second sensor does not exceed a safe temperature level, and ii) monitor said outlet gases temperature sensor and said ambient air temperature sensor, compare said outlet gases temperature and said ambient air temperature and when these are substantially equal end said predetermined time and switch of said gases supply means and said pathway heater.

Preferably said transportation pathway means has a pathway heater, and said apparatus further comprises: a) a distal temperature sensor measuring the temperature of said gases at the distal end of the transportation pathway means, b) an ambient temperature sensor measuring ambient air temperature, c) a chamber heater temperature sensor measuring said chamber heater temperature, and said controller includes stored instructions to: i) control said pathway heater over said predetermined time such that the temperature of said gases at the distal end of said transportation pathway means, as sensed by said second sensor does not exceed a safe temperature level, and ii) monitor said chamber heater temperature sensor and ambient air temperature sensor, compare said chamber heater temperature and said ambient air temperature and when these are substantially equal end said predetermined time and switch off said gases supply means and said pathway heater.

Preferably said transportation pathway means is an extruded plastic tube, and said pathway heater is at least two conductive wires embedded within, throughout or about the wall of said tube.

Preferably said controller includes stored instructions to determine said end of said treatment when said patient activates an "off" button connected to said controller.

Alternatively said apparatus further comprises a patient interface sensor, and said controller includes stored instructions to determine said end of said treatment when said patient interface sensor detects that said patient has removed said patient interface for a predetermined period of time.

Alternatively said controller includes stored instructions to determine said end of treatment when a substantial increase of flow of gases is detected exiting said gas supply means for a predetermined period of time.

Alternatively said apparatus further comprises a patient interface sensor, and said controller includes stored instructions to determine said end of treatment when said patient interface sensor senses that said patient's breathing through said patient interface has ceased for a predetermined period of time.

In a second aspect the present invention consists in a method of controlling a breathing assistance apparatus where said apparatus is adapted to deliver humidified gases at a desired level of humidity, flow and temperature for treatment of a patient, said apparatus comprising a gases supply means providing a flow of gases, a humidifier having a chamber adapted to receive a volume of water and a chamber heater to heat said water in said chamber, transportation pathway means to convey said humidified gases from said humidifier to said patient, and a controller that stores a program which causes the controller at the end of said treatment of said patient to: a) switch off power to said chamber heater, b) set said flow of gases from said gases supply means to a predetermined flow for a predetermined time, c) after said predetermined time switch off said gases supply means.

Preferably said transportation pathway means has a pathway heater, and said apparatus further comprises an outlet temperature sensor measuring the temperature of said gases at said outlet to said chamber, a distal temperature sensor measuring the temperature of said gases at the distal end of the transportation pathway means, an ambient temperature sensor measuring ambient air temperature, and said program further causes said controller to: a) control said pathway heater over said predetermined time such that the temperature of said gases at the distal end of said transportation pathway means, as sensed by said second sensor does not exceed a safe temperature level, and b) monitor said outlet gases temperature sensor and said ambient air temperature sensor, compare said outlet gases temperature and said ambient air temperature and when these are substantially equal end said predetermined time and switch of said gases supply means and said pathway heater.

Preferably said transportation pathway means has a pathway heater, and said apparatus further comprises a distal temperature sensor measuring the temperature of said gases at the distal end of the transportation pathway means, an ambient temperature sensor measuring ambient air temperature, a chamber heater temperature sensor measuring said chamber heater temperature, and said program further causes said controller to: a) control said pathway heater over said predetermined time such that the temperature of said gases at the distal end of said transportation pathway means, as sensed by said second sensor does not exceed a safe temperature level, and b) monitor said chamber heater temperature sensor and ambient air temperature sensor, compare said chamber heater temperature and said ambient air temperature and when these are substantially equal end said predetermined time and switch off said gases supply means and said pathway heater.

Preferably said program further causes said controller to determine said end of said treatment when said patient activates an "off" button connected to said controller.

Alternatively said apparatus further comprises a patient interface sensor and said program further causes said controller to determine said end of said treatment when said patient interface sensor detects that said patient has removed said patient interface for a predetermined period of time.

Alternatively said program further causes said controller to determine said end of treatment when a substantial increase of flow of gases is detected exiting said gas supply means for a predetermined period of time.

Alternatively said apparatus further comprises a patient interface sensor and said program further causes said controller to determine said end of treatment when said patient interface sensor senses that said patient's breathing through said patient interface has ceased for a predetermined period of time.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

Preferred forms of the present invention will now be described with reference to the accompanying drawings.

FIG. 1 is an illustration of the breathing assistance apparatus that the control method of the present invention may be used with.

DETAILED DESCRIPTION OF THE PREFERRED EMBODIMENT

A breathing assistance apparatus and method of controlling a breathing assistance apparatus is detailed below. Particularly, the breathing assistance apparatus is controlled such that it has a drying cycle to enable drying of the tubing that supplies gases to a user and prevent the harbouring of pathogens within the tube. The drying cycle is preferably operated automatically by internal controllers in the apparatus. However, it may be manually activated by pressing a button on the apparatus. The drying cycle is preferably activated at the end of a patient's treatment session.

The breathing assistance apparatus of the present invention is intended to typically deliver body temperature saturated gases (37.degree. C. and 44 mg/L) over a range of flows that could provide up to a patient's inspiratory flow requirements (that is, peak inspiratory flow) plus any bias flow requirement.

The breathing assistance apparatus operates as a flow controlled device, so it adjusts the flow of gases to the level set by the patient or user, such as a care giver. Therefore, this apparatus can be used to deliver humidified gas for patients with bypassed airways, such as tracheotomies or nasal cannula or masks.

Whether used in a hospital environment or in a home care environment, the breathing assistance apparatus of the present invention will generally have associated with it a gases supply means, such as ambient air, gases, such as oxygen from cylinders or other compressed gas supply, humidification means and a transport conduit from the humidification means to the patient, which is preferably heated to reduce condensation.

A heating element is preferably provided within the transport conduit to help prevent condensation of the humidified gases within the conduit. Such condensation is due to the temperature of the walls of the conduit being lower than to the dew point of the gases inside the conduit, which is usually lower than the temperature of the humidified gases within the conduit. The heating element effectively replaces the energy lost from the gases through conduction and convection during transit through the conduit and the patient interface. Thus the conduit heating element ensures the gases delivered are at an optimal temperature and humidity for patient treatment and to minimise condensation within the transport conduit and the patient interface.

Figure 1:
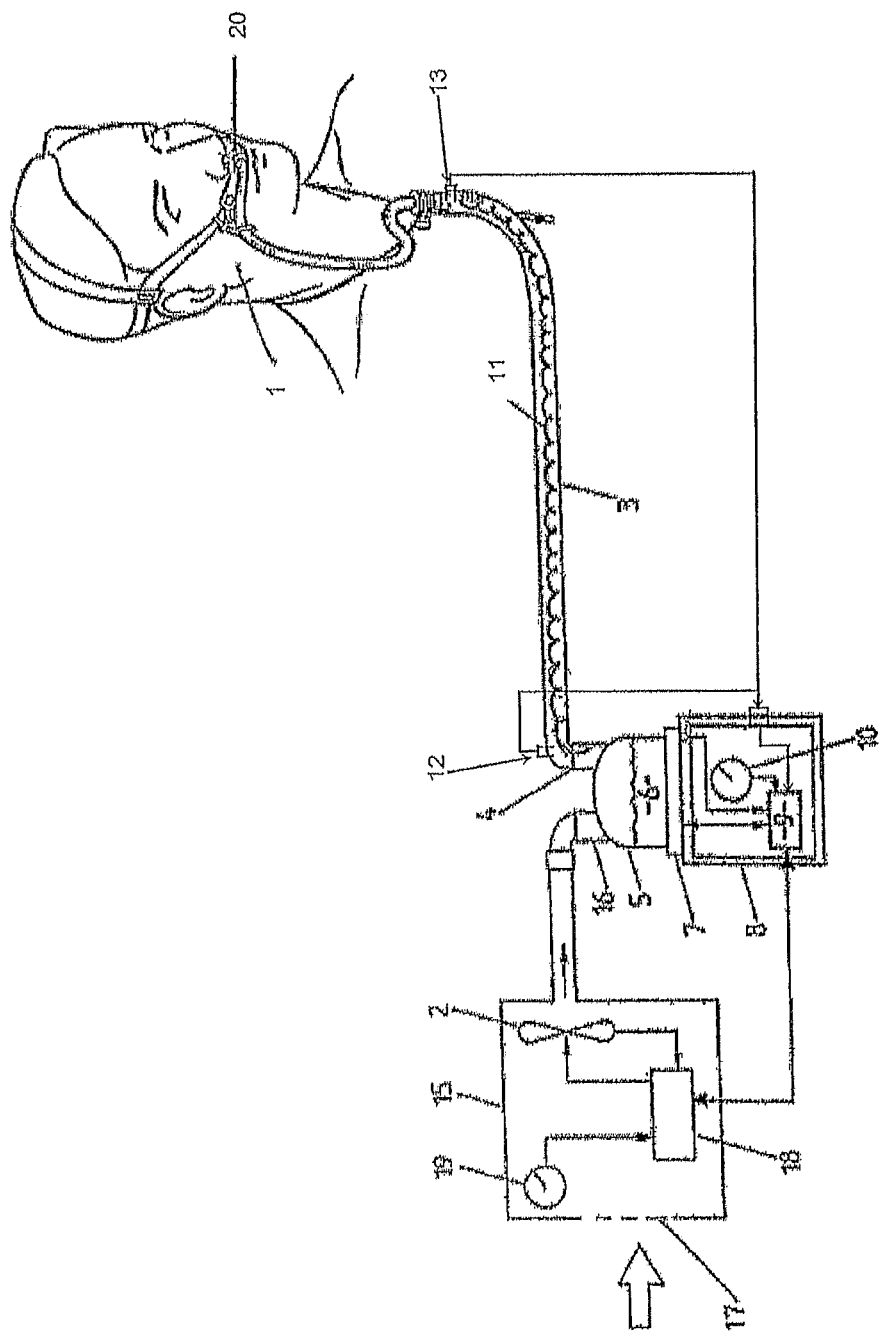

The present invention provides a breathing assistance apparatus where the flow of gases passes in sequence through a gases supply means or flow driver (such as, a blower, fan or compressor), humidification chamber, heated delivery circuit and patient interface, such as that shown in FIG. 1.

With reference to FIG. 1 the humidification apparatus of the present invention is shown in which a patient 1 is receiving humidified and pressurised gases through a nasal cannula 20 connected to a humidified gases transportation pathway or inspiratory conduit 3 that in turn is connected to a humidifier 8 (including humidification chamber 5) that is supplied with gases from a blower 15 or other appropriate gases supply means. The inspiratory conduit 3 is connected to the outlet 4 of a humidification chamber 5 which contains a volume of water 6. Inspiratory conduit 3 contains heating means or heater wires 11 that heat the walls of the conduit to reduce condensation of humidified gases within the conduit and the patient interface (e.g. nasal cannula 20). The humidification chamber 5 is preferably formed from a plastics material and may have a highly heat conductive base (for example an aluminium base) which is in direct contact with a heater plate 7 of humidifier 8. The humidifier 8 is provided with control means or electronic controller 9 which may comprise a microprocessor based controller executing computer software commands stored in associated memory.

Gases flowing through the inspiratory conduit 3 are passed to the patient by way of a patient interface 20. The patient interface used with the apparatus of the present invention may be a full-face mask, nasal mask, nasal cannula, oral mouthpiece or tracheostomy connection.

Controller 9 receives input from sources such as user input means or dial 10 through which a user of the device may, for example, set a predetermined required value (preset value) of humidity or temperature of the gases supplied to patient 1. In response to the user set humidity or temperature value input via dial (or buttons) 10 and other possible inputs such as internal sensors that sense gases flow or temperature, or by parameters calculated in the controller, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber 5 through inlet 16. It should be noted that it is possible to obtain the relationship between the humidity of the gases in humidification chamber 5 and the temperature of the heater plate 7. Accordingly, it is possible to utilise the heater plate temperature in an algorithm or a look-up table to determine the humidity of the gases.

It is also possible to measure the chamber outlet gases temperature from the humidification chamber 5 using a temperature sensor 12 and use this to determine the humidity of the gases in the chamber 5 and conduit 3.

The blower 15 may be provided with a variable speed pump or fan 2 which draws air or other gases through the blower inlet 17. The speed of variable speed pump or fan 2 may be controlled by a further control means or electronic controller 18 (or alternatively the function of this controller 18 could be carried out by the other controller 9) in response to inputs from controller 9 and a user set predetermined required value (preset value) of pressure or fan speed via dial 19.

Figure 2:
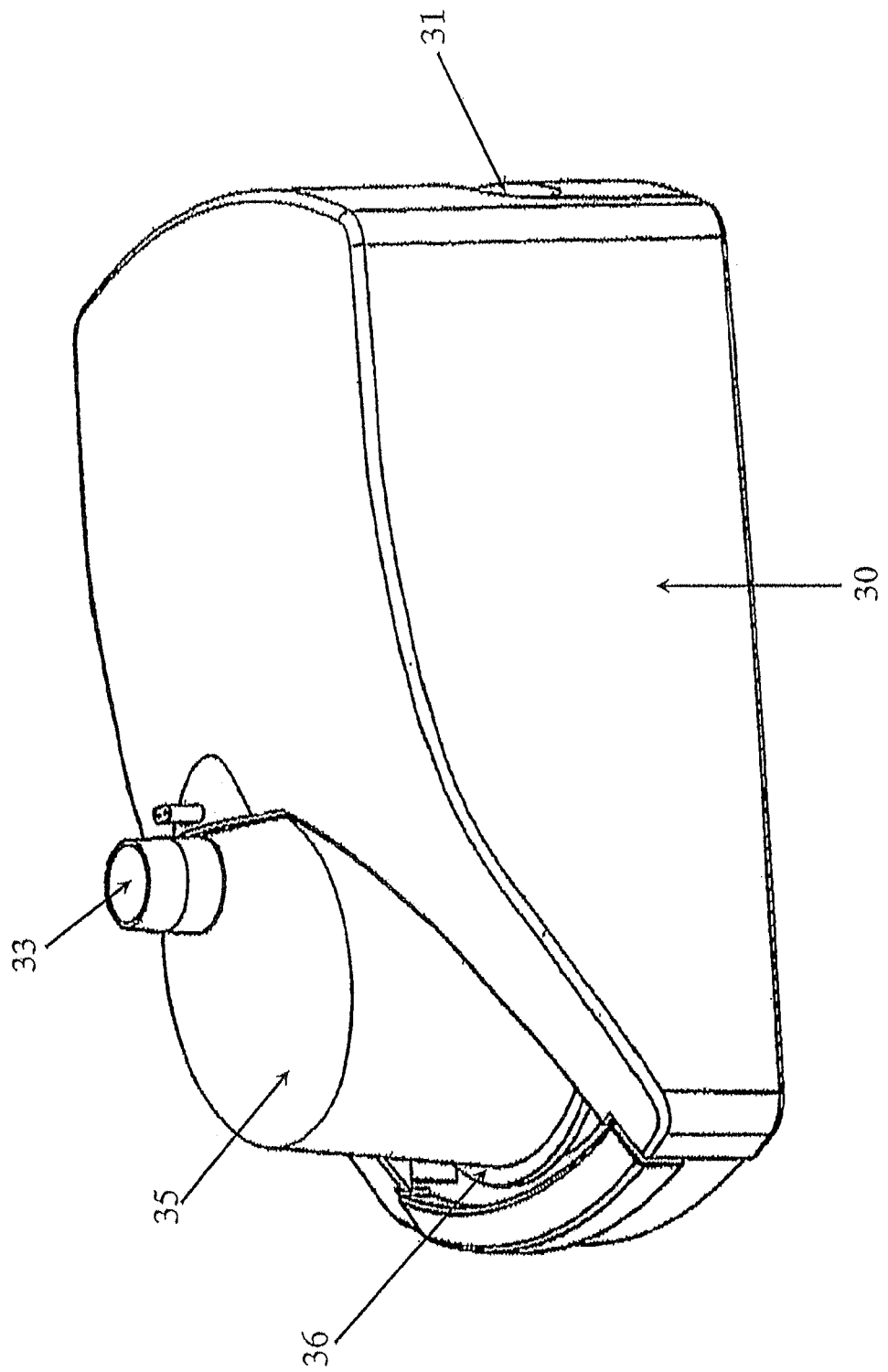
FIG. 2 is a perspective view of a combined gases supply and humidifier of the breathing assistance apparatus of the present invention.

In the preferred embodiment shown in FIG. 2 the breathing assistance apparatus of the present invention the gases supply or blower is combined in one housing with the humidifier and humidification chamber. The humidification chamber 35 extends out from the housing 30 and is capable in use of being removed and replaced by the patient or other user. Also, the inlet port (not shown) to the humidification chamber 35 is internal within the housing 30. The inlet 31 to the housing 30 where gases are drawn from the ambient air outside the housing 30 is located at the end of the housing 30, but in actuality may be located at any appropriate point in the housing 30. The gases exit from the humidification chamber 35 at the outlet 33 and water within the chamber 35 is heated by a heater plate 36, similar to that described above. It must be appreciated that the embodiment described above in relation to the housing and FIG. 2 merely illustrates one form of the housing of the combined gases supply and humidifier of the present invention.

In one preferred form of the apparatus of the present invention, a nasal cannula 20 is used as the patient interface. The initial connection of a patient 1 to a blower and humidifier is an obstacle to patient compliance and negates a patient's comfort and tolerance due to the high pressure supply of gases through the cannula. Therefore, it would be advantageous if the gases flow was slowly increased to the patient, allowing their body time to adjust to the temperature, sensation of flow, and pressure in their nasopharynx. This slow increase in flow may be over a considerable time, such as 30 minutes, allowing the patient to slowly adjust to the therapy instead of feeling overwhelmed with the sudden delivery to the nasal passage, of up to 40 L/min of saturated gases.

As discussed earlier, high flows of non-humidified gases delivered to the patients airways causes dehydration and inflammation of the airways and nasal passages. At low flows (such as 5 litres per minute) a lower level of humidity is adequate. Because an active pass-over humidifier 8 holds a humidification chamber 5 which contains a volume of water 6, this water has a large thermal mass and takes time to heat up enough to provide adequate humidity at high flows.

Warm Up Mode

The blower 15 may be controlled by a controller (18 or 9) such that on start-up or commencement of therapy by the patient 1 the flow rate of gases exiting the blower 15 is initially supplied as a low flow.

Under the warm up mode the aim is to deliver optimal gas to the patient. To do this, it is necessary to warm up the gases in the chamber as quickly as possible to a set value, most preferably 37.degree. C. As the temperature of the gases at the chamber outlet are measured by a sensor this is the temperature that is to be controlled to the set temperature value. In this way the patient is supplied with an optimal temperature of gases as soon as possible. This is achieved by; turning on the heater plate 7 to full heating output, providing a low flow of gases through the humidification chamber 5 and controlling the wall temperature of the heated conduit 3 to avoid condensation. When the gases temperature in the humidification chamber 5 reaches the set temperature the gases flow is increased to the predetermined therapy flow as fast as possible, while maintaining the gases temperature in the chamber at the set temperature. The increasing of the gases flow is performed by controlling (increasing) the speed of the fan 21 in the blower 15. Alternatively, when the water chamber gases reach the set temperature the flow is increased to the target or predetermined flow for the therapy. As soon as the gases temperature in the water chamber recovers to approximately the set temperature, for example, 35.degree. C., a signal is given by the controller that the patient can now wear the interface.

As an example, gases flow is increased from the initial low flow (flow.sub.initial) to a flow that is optimal (flow.sub.opt) for the therapy being provided. It is preferred that the maximum or optimum flow level (flow.sub.opt) is selectable by the user or care provider by way of dial 19. In this case, the controller 18 or 9 would control the flow rate, by controlling the fan 21 speed so that the gases flow is initially at a low flow rate of, for example, 5 L/min. Alternatively, the gases flow could be switched on for, for example, 1 to 15 seconds, at a low flow of, for example, 5 L/min to allow the temperature and humidity readings to be taken. Then the gases flow would be switched off for a period of time, for example, 5 to 60 seconds, to allow the humidity in the chamber to rise quicker.

Once the temperature the gases exiting the humidifier chamber reaches 37.degree. C. (the set temperature), the flow of the gases is ramped up over a predetermined time, for example, 30 minutes, to an optimum flow level (flow.sub.opt) of between 15 to 40 L/min, as selected by the patient.

The above sequence of events enables the humidity in the breathing circuit to reach the desired level as quickly as possible while minimising condensation and/or thermal overshoot.

Drying Mode

To overcome the problem of any condensation left in the conduit 3 or in the patient interface 20 at the end of a therapy treatment session, the breathing assistance apparatus of the present invention provides a mode or cycle of drying out the conduit 3 and potentially the interface 20. This is carried out by providing a turn off process that facilitates the drying of the conduit 3 and the patient interface 20.

A drying mode is critical in minimising the risk of pathogen transport via the conduit 3 and interface 20 to the patient 1. A drying mode also ensures there will be no condensation left in the conduit or patient interface after a treatment session and in a next treatment session. Condensation can cause gurgling noises and surges in airflow at the beginning of the next humidification session making treatment uncomfortable for the patient.

Generally, the aim of the drying mode is to ensure the humidity of the gases in the chamber and conduit are at or below the ambient levels the apparatus is operating in. This is achieved by cooling the water in the humidification chamber 5, while continuing to heat the conduit 3 and the interface 20 to a temperature that exceeds the chamber outlet gases temperature. This is continued until the humidifier water temperature and temperature of the gases at the chamber outlet reach or approximate room temperature. As the thermal mass of the water in the chamber 5 exceeds the thermal mass of the plastic walls of the conduit 3, condensation may occur if the humidifier 8 and the blower fan 21 are turned off at the same time. To ensure this does not occur, at the end of treatment it is preferred that the heater plate 7 is turned off but power is maintained to a heater wire 11 in the conduit 3.

The humidification means, humidifier 8, is controlled by the control means (controller 9 or 18) at the completion of a patient's treatment. Therefore, when the patient selects "off", a button on the apparatus, or the controller detects the end of a therapy session, effectively only the heater plate 7 is powered down by the controller (9 or 18) and the humidification apparatus is placed in a drying mode. During the drying mode, it is preferred that power is maintained to the heater wire 11 and the gases supply means or blower 15. As an example, the gases flow through the humidifier 8 and conduit 3 is a flow, such as 20 litres per minute for a period of time, for example 15 minutes, which will ensure the conduit has dried inside. The gases flow may be a fixed gases flow or pulses of gases flow.

A temperature sensor 13 is preferably provided at the end of the conduit, nearest the patient. This end of conduit temperature sensor 13 is connected to the controller 9, 18. The end of conduit sensor 13 may be used to optimise drying of the conduit 3 by ensuring the gases at the end of the breathing circuit are at the maximum safe operating temperature, so that the temperature of the gases does not obtain a level that might burn a patient or user.

Preferably it might be optimal to start at a low gases flow and then at a later stage increase the gases flow.

In some forms of the present invention the conduit may not include a heater wire. In this situation the controller would merely control the blower 15, such that gases and not heat from the heater wire within the conduit alone would dry the conduit.

Deactivation of Drying Mode

The point in time that the drying mode is deactivated may be determined by a number of methods. The first of which is to measure the temperature of gases at the chamber outlet 4. When the temperature of the gases at the chamber outlet 4 drops below or equals ambient temperature (which is preferably measured by an additional temperature sensor, for example, located at the blower 15 but connected to one of the controllers 9, 18) the blower 15 and heater wire 11 are powered off by the controller 9, 18. In this way gases flow through the humidification chamber 6 and as the heater plate 7 cools the humidity of the gases flowing through the conduit 3 reduces and the conduit 3 becomes drier.

A second method for determining when the drying mode is to be deactivated by the controller 9, 18 is to turn off the power to the humidification chamber 5 and maintain a gases flow through the conduit 3 at a fixed speed or pulses and maintain power in the heater wire 11 to evaporate any condensate off the walls of the conduit 3. After a predetermined time, preferably in excess of one minute, the heater wire 11 and flow source (blower) would be switched off.

Yet another method of controlling the drying of the conduit is to switch the gases supply (blower) off and switch off the power to the heater plate power. The controller 9, 18 would then compare the heater plate 7 temperature with an ambient temperature that is measured either inside or outside the humidifier or blower (as previously described). When this temperature difference or comparison is within a predetermined limit, which typically approximates zero, a flow of gases is caused to flow in the same manner as described above.

It is possible that it could take longer to dry the condensate in the conduit than to cool the chamber. In this instance it may be necessary to extend the drying mode for some time, for example, up to 30 minutes depending on the ambient temperature of the water remaining in the chamber.

Alternative Methods of Activation of Drying Mode

It has been described that the drying mode is activated by the patient selecting or pressing an "off" button. An alternative method of activating the drying mode is to detect the patient 1 removing the interface 20. This may be, for example, by detecting an increase in the flow from the blower due to decreased resistance at the patient interface at the end of a humidification session. After a predetermined time period has elapsed, which is long enough to ensure the patient does not put the interface back on, the drying mode is commenced.

As a further alternative method the time at which the patient stops breathing into the patient interface 20 may be detected. This may be detected by monitoring for a breathing pattern, for example using a flow sensor on the patient interface or in the blower. Once no breathing is found and after waiting a predetermined time period the drying mode is commenced.

In order for the apparatus to be fully powered down a user or patient must disconnect the apparatus from the electrical power supply or for example, hold a switch or power button down on the humidifier or blower for a period of time, for example, 5 seconds.

What is claimed is:

1. A breathing assistance apparatus comprising:
a gases supply adapted to provide a flow of gases;
a humidifier having a chamber heater;
a controller comprising memory with computer-executable instructions stored thereon and a processor, wherein the computer-executable instructions, when executed, cause said controller to:
monitor for a breathing pattern,
in response to no breathing pattern detected for a first predetermined time period:
switch off power to said chamber heater,
control the gases supply to set said flow of gases from said gases supply for a second predetermined time, and
after said second predetermined time, switch off said gases supply; and
a second heater separate from said chamber heater, the second heater configured to heat said flow of gases for at least a portion of said second predetermined time.

2. A breathing assistant apparatus according to claim 1, further comprising a flow sensor in communication with the controller, wherein the computer-executable instructions, when executed, further cause said controller to monitor for said breathing pattern based on flow measurements from the flow sensor.

3. A breathing assistant apparatus according to claim 1, further comprising a transportation pathway, wherein said second heater is a pathway heater configured to heat the transportation pathway.

4. A breathing assistant apparatus according to claim 3, wherein the computer-executable instructions, when executed, further cause said controller to control the gases supply to vary said flow of gases during said second predetermined time to evaporate condensate from the transportation pathway.

5. A breathing assistant apparatus according to claim 4, wherein the computer-executable instructions, when executed, further cause said controller to control the gases supply to increase said varied flow of gases from a first gases flow to a second gases flow within said second predetermined time to evaporate condensate from the transportation pathway.

6. A breathing assistant apparatus according to claim 4, wherein the computer-executable instructions, when executed, further cause said controller to control the gases supply to pulse said varied flow of gases within at least a portion of said second predetermined time to evaporate condensate from the transportation pathway.

7. A breathing assistant apparatus according to claim 3, wherein the computer-executable instructions, when executed, further cause said controller to control the gases supply to set a fixed speed of said flow of gases through the transportation pathway.

8. A breathing assistance apparatus according to claim 1, wherein the computer-executable instructions, when executed, further cause said controller to determine an end of treatment when said patient activates an off button connected to said controller.

9. A breathing assistant apparatus according to claim 1, further comprising a flow sensor adapted to detect said breathing pattern by detecting flow patterns.

10. A breathing assistant apparatus according to claim 9, wherein the gases supply comprises a blower, and wherein said flow sensor is disposed in or adjacent the blower.

11. A breathing assistant apparatus according to claim 9, wherein further comprising a patient interface coupled to or fluidically connected to a transportation pathway and wherein said flow sensor is disposed on the patient interface.

12. A breathing assistant apparatus according to claim 1, wherein the computer-executable instructions, when executed, further cause said controller to control the gases supply to set a constant flow of said flow of gases during said second predetermined time.

13. A breathing assistant apparatus according to claim 1, wherein the computer-executable instructions, when executed, further cause said controller to control the gases supply to pulse said flow of gases during said second predetermined time.

14. A method comprising:
supplying a flow of gases from a gases supply;
heating a humidifier with a chamber heater;
as performed by a controller comprising a processor and memory:
monitoring for a breathing pattern,
in response to no breathing pattern detected for a first predetermined time period:
switching off power to said chamber heater,
controlling the gases supply to set said flow of gases from said gases supply for a second predetermined time, and
after said second predetermined time, switching off said gases supply; and
heating said flow of gases for at least a portion of said second predetermined time using a heater separate from said chamber heater.

15. A method according to claim 14, further comprising detecting the breathing pattern using a flow sensor.

16. A method according to claim 14, further comprising heating a transportation pathway with the separate heater.

17. A method according to claim 14, further comprising, as performed by the controller, controlling the gases supply to vary said flow of gases during said second predetermined time.

18. A method according to claim 14, further comprising, as performed by the controller, controlling the gases supply to increase said flow of gases from a first gases flow to a second gases flow within said second predetermined time.

* * * * *

UNITED STATES PATENT AND TRADEMARK OFFICE
CERTIFICATE OF CORRECTION

PATENT NO. : 10,918,821 B2  
APPLICATION NO. : 15/811308  
DATED : February 16, 2021  
INVENTOR(S) : Matthew Jon Payton Page 1 of 1

It is certified that error appears in the above-identified patent and that said Letters Patent is hereby corrected as shown below:

On the Title Page

Inventors, Item (72), delete "Virgina Louise Owen" and insert --Virginia Louise Owen--.

In the Claims

In Column 11, Line 21, Claim 2, delete "breathing assistant apparatus" and insert --breathing assistance apparatus--.

In Column 11, Line 27, Claim 3, delete "breathing assistant apparatus" and insert --breathing assistance apparatus--.

In Column 11, Line 31, Claim 4, delete "breathing assistant apparatus" and insert --breathing assistance apparatus--.

In Column 11, Line 37, Claim 5, delete "breathing assistant apparatus" and insert --breathing assistance apparatus--.

In Column 11, Line 44, Claim 6, delete "breathing assistant apparatus" and insert --breathing assistance apparatus--.

In Column 11, Line 50, Claim 7, delete "breathing assistant apparatus" and insert --breathing assistance apparatus--.

In Column 12, Line 1, Claim 8, delete "breathing assistant apparatus" and insert --breathing assistance apparatus--.

In Column 12, Line 6, Claim 9, delete "breathing assistant apparatus" and insert --breathing assistance apparatus--.

Signed and Sealed this  
Sixth Day of July, 2021

Drew Hirshfeld  
*Performing the Functions and Duties of the*  
*Under Secretary of Commerce for Intellectual Property and*  
*Director of the United States Patent and Trademark Office*